US012577541B2

(12) United States Patent
Hong et al.

(10) Patent No.: US 12,577,541 B2
(45) Date of Patent: *Mar. 17, 2026

(54) METHOD FOR LARGE-SCALE PREPARATION OF PURIFIED PREPARATION OF RECOMBINANT LENTIVIRAL VECTOR AT GMP GRADE

(71) Applicant: ABELZETA INC., Rockville, MD (US)

(72) Inventors: Yi Hong, Shanghai (CN); Ting Yan, Shanghai (CN); Jiangguo Ying, Shanghai (CN); Haojie Zhang, Shanghai (CN); Li Zhang, Shanghai (CN); Fei Wang, Shanghai (CN); Dijun Zhao, Shanghai (CN); Luyi Zhang, Shanghai (CN)

(73) Assignee: ABELZETA INC., Rockville, MD (US)

( * ) Notice: Subject to any disclaimer, the term of this patent is extended or adjusted under 35 U.S.C. 154(b) by 1292 days.

This patent is subject to a terminal disclaimer.

(21) Appl. No.: 17/034,168

(22) Filed: Sep. 28, 2020

(65) Prior Publication Data

US 2021/0147826 A1 May 20, 2021

Related U.S. Application Data

(63) Continuation of application No. PCT/CN2019/080213, filed on Mar. 28, 2019.

(30) Foreign Application Priority Data

Mar. 28, 2018 (CN) ......................... 201810264813.X

(51) Int. Cl.
| | |
|---|---|
| *C12N 7/02* | (2006.01) |
| *C12M 1/00* | (2006.01) |
| *C12N 7/00* | (2006.01) |
| *C12N 15/10* | (2006.01) |
| *C12N 15/86* | (2006.01) |

(52) U.S. Cl.
CPC ............... *C12N 7/02* (2013.01); *C12M 47/02* (2013.01); *C12M 47/12* (2013.01); *C12N 7/00* (2013.01); *C12N 15/101* (2013.01); *C12N 15/1017* (2013.01); *C12N 15/86* (2013.01); *C12N 2740/15021* (2013.01); *C12N 2740/15043* (2013.01); *C12N 2740/15051* (2013.01)

(58) Field of Classification Search
None
See application file for complete search history.

(56) References Cited

U.S. PATENT DOCUMENTS

| | | |
|---|---|---|
| 2003/0175688 A1 | 9/2003 | Pennathur-Das et al. |
| 2007/0249019 A1 | 10/2007 | Kang et al. |
| 2008/0026448 A1 | 1/2008 | Lyderson et al. |
| 2009/0175906 A1 | 7/2009 | Kaylan et al. |
| 2011/0207202 A1 | 8/2011 | Luitjens et al. |
| 2014/0315294 A1 | 10/2014 | Marceau et al. |
| 2015/0133636 A1 | 5/2015 | Xenopoulos et al. |
| 2017/0002332 A1 | 1/2017 | Boudeffa et al. |

FOREIGN PATENT DOCUMENTS

| | | | | |
|---|---|---|---|---|
| CN | 103881984 A | 6/2014 | | |
| CN | 104371982 A | 2/2015 | | |
| CN | 106434571 A | 2/2017 | | |
| CN | 106474466 A | 3/2017 | | |
| CN | 107043784 A | * 8/2017 | ............ | C12N 15/86 |
| CN | 107384877 A | 11/2017 | | |
| CN | 107523555 A | 12/2017 | | |
| CN | 107630037 A | 1/2018 | | |
| CN | 107841482 A | 3/2018 | | |
| JP | 2009-534030 A | 9/2009 | | |
| JP | 2017-503486 A | 2/2017 | | |
| JP | 2018-507707 A | 3/2018 | | |
| WO | 0009671 A1 | 2/2000 | | |
| WO | 03/039459 A2 | 5/2003 | | |
| WO | 2013/076309 A1 | 5/2013 | | |
| WO | WO-2014145578 A1 * | 9/2014 | ....... | A61K 480/0091 |
| WO | 2016/128408 A | 5/2016 | | |

OTHER PUBLICATIONS

Cai et al. PLoS One. 2015; 10(8): e0136741, PMID: 26305356.. (Year: 2015).*
Merten et al., "Production of lentiviral vectors," Molecular Therapy—Methods & Clinical Development, 3: 16017 (Year: 2016).*
Cooper et al., "Highly Efficient Large-Scale Lentiviral Vector Concentration by Tandem Tangential Flow Filtration," J Virol Methods 177(1): 1-9 (Year: 2011).*
Negrete et al., "Use of hollow fiber tangential flow filtration for the recovery and concentration of HIV virus-like particles produced in insect cells," Journal of Virological Methods 195: 240-246 (Year: 2014).*
Maria Mercedes Segura et al: "New developments in lentiviral vector design, production and purification", Expert Opinion on Biological Therapy, vol. 13, No. 7, 2013, pp. 987-101.

(Continued)

*Primary Examiner* — M Franco G Salvoza
(74) *Attorney, Agent, or Firm* — LEASON ELLIS LLP

(57) ABSTRACT

Provided is a method for large-scale preparation of a purified preparation of a recombinant lentiviral vector at the GMP grade. The method comprises: (a) providing raw material feed liquid to be purified that comprises recombinant viral vectors; (b) carrying out a microfiltration treatment on the feed liquid to obtain a microfiltered filtrate comprising the recombinant viral vectors; (c) optionally concentrating the filtrate to obtain a concentrated filtrate; (d) purifying the filtrate obtained in the previous step by means of chromatography to obtain a crude pure product comprising the recombinant viral vectors; and (e) subjecting the crude pure product obtained in the previous step to liquid exchange and elaborate purification to obtain the purified recombinant viral vectors.

7 Claims, No Drawings

(56)                    References Cited

OTHER PUBLICATIONS

Ansorage S et al: "Development of a scalable process for high-yield lentiviral vector production by transient transfection of HEK293 suspension cultures", The Journal of Gene Medicine, vol. 11, No. 10, 2009, pp. 868-876.

Broussau et al.: "Inducible Packaging Cells for Large-scale Production of Lentiviral Vectors in Serum-free Suspension Culture", Molecular Therapy, 2008, 16(3): 500-507.

Segura et al.: "Production of Lentiviral Vectors by Large-Scale Transient Transfection of Suspension Cultures and Affinity Chromatography Purification", Biotechnology and Bioengineering, 2007, 98(4): 789-799.

Cai et al.: Lentiviral Vector Packaging and Production Method, Journal of Yangtze University, Natural Science Edition, 2014, vol. 11, No. 9, pp. 121-123.

Bandeira et al. Downstream Processing of Lentiviral Vectors: Releasing Bottlenecks, Human Gene Therapy Methods, 2012, vol. 23, No. 4, pp. 255-263.

International Search Report and Written Opinion in PCT/CN2019/080213, mailed on May 30, 2019.

Ansorge et al. Recent progress in lentiviral vector mass production, Biochemical Engineering Journal, 2010, vol. 48, No. 3, pp. 362-374.

International Search Report and Written Opinion in PCT/CN2019/080215, mailed on May 24, 2019.

U.S. Appl. No. 17/041,578 (371 of PCT/CN2019/080215 (WO2019/184996)), in Chinese and English.

Jiang et al., Purification of Rotavirus by using Multimode media Capto core 700, Chinese J. Biologicals, 2015, vol. 28 No. 1, pp. 72-78.

Witting et al: "Efficient Large Volume Lentiviral Vector Production Using Flow Electroporation", Human Gene Therapy, 2012, vol. 23, pp. 243-249.

* cited by examiner

METHOD FOR LARGE-SCALE PREPARATION OF PURIFIED PREPARATION OF RECOMBINANT LENTIVIRAL VECTOR AT GMP GRADE

TECHNICAL FIELD

The present invention relates to the technical field of biology, particularly to a method for large-scale preparation of a purified preparation of a recombinant lentiviral vector at the GMP grade.

BACKGROUND TECHNOLOGIES

Gene therapy refers to introducing exogenous therapeutic genes into target cells to correct or compensate for diseases caused by gene defects and abnormalities, or acting on disease targets through products expressed by exogenous genes to achieve the purpose of treatment.

Exogenous genes can be transduced or delivered by viral vectors or non-viral vectors. The popular non-viral vectors include liposomes, dendrimers, non-natural cationic polymers, natural polysaccharides, etc. Non-viral gene delivery vectors are relatively safe and stable, but their transfection efficiency is low normally in general. Viral vectors package exogenous genes into the outer shell of natural viruses and use the infectivity of the viruses to host cells to introduce exogenous genes into cells. Common viral vectors include recombinant retrovirus (rRV), recombinant lentivirus (rLV), recombinant adenovirus (rAd), recombinant adeno-associated virus (rAAV), etc. Viral vectors have transduction efficiency much higher than that of non-viral vectors and are especially suitable for infecting target cells that are difficult to infect, such as lymphocytes.

Recombinant lentiviral vectors are gene therapy vectors developed based on HIV-1 (human immunodeficiency virus-1). Different from the general retroviral vectors, the recombinant lentiviral vectors have the ability to infect both dividing and non-dividing cells. The recombinant lentiviral vectors have become the preferred transgenic vectors for CART cells and gene therapy due to their high biological titer in vivo and in vitro, low immunogenicity and other advantages.

The current recombinant lentiviral vectors use a method of genetic modification to leave only the packaging signals and the original transcription of the target gene in the lentiviral genome, disperse the reverse transcriptase, envelope protein VSVG, gag-pol and other structural genes in 2 to 3 vectors and delete the pathogenic genes at the same time. Mature lentiviral particles are produced by co-transfecting multiple vectors into 293T cells and then packaged in the cells, and are secreted from 293T cells into the culture supernatant, which can be obtained by ultracentrifugation or chromatographic purification.

A method used in conventional laboratories to obtain lentiviruses is ultracentrifugation. This method is simple, but it cannot be industrially enlarged, and the prepared lentiviral vector may contain high levels of endotoxin, BSA, HCP or nucleic acid and other residues and cannot be used directly in the human body.

Further, the existing chromatographic purification methods also have the disadvantages of complicated steps, a low yield and insufficient purity and can hardly meet the requirements of industrial large-scale production and GMP-grade production.

Therefore, there is an urgent need in this field to develop a new and efficient method for preparing purified lentiviral vectors, which is suitable for large-scale production and meets the requirements of GMP-grade production.

SUMMARY

An object of the present invention is to provide an efficient method for preparing purified lentiviral vectors, which is suitable for large-scale production and meets the requirements of GMP-grade production.

Another object of the present invention is to provide recombinant lentiviruses purified by the method, and a purified preparation containing the recombinant lentiviruses and the application thereof.

In a first aspect of the present invention, a method for large-scale purification of a recombinant viral vector preparation is provided. The method comprises the following steps:

(a) Providing a raw material, which comprises recombinant viral vectors to be purified and is a feed liquid in a volume of $V_a$;

(b) Carrying out a microfiltration treatment on the feed liquid to obtain a microfiltered filtrate, which comprises the recombinant viral vectors and is in a volume of $V_b$;

(c) Optionally concentrating the filtrate to obtain a concentrated filtrate in a volume of $V_c$;

(d) Purifying the filtrate obtained in the previous step by means of chromatography to obtain a crude pure product comprising the recombinant viral vectors; and (e) Subjecting the crude pure product obtained in the previous step to liquid exchange and elaborate purification to obtain purified recombinant viral vectors.

Here, the chromatography is selected from anion chromatography, molecular exclusion chromatography and multimodal composite resin chromatography, or a combination thereof.

In another preferred embodiment, the $V_a \geq 100$ L (or 100 to 500 L).

In another preferred embodiment, after the step (e), the method further comprises:

(f) subjecting the purified recombinant viral vectors to liquid exchange to replace the purified recombinant viral vectors into a virus freezing medium containing the recombinant viral vectors;

(g) Filtering and sterilizing the virus after the solution replacement to obtain sterilized recombinant viral vectors.

In another preferred embodiment, the virus includes lentivirus.

In another preferred embodiment, the method is in compliance with GMP conditions.

In another preferred embodiment, in the step (d), molecular exclusion chromatography and anion chromatography are performed in turn, successively or simultaneously.

In another preferred embodiment, the anionic resin is selected from: CAPTO™ Q CAPTO™ ImpRes and CAPTO™ DEAE. CAPTO™ is a type of chromatography resin.

In another preferred embodiment, multimodal composite chromatography resin: CAPTO™ adhere ImpRes or CAPTO™ core 700 is adopted.

In another preferred embodiment, the purification by means of chromatography is to perform primary purification by means of anion chromatography first and then perform elaborate purification by means of multimodal composite chromatography.

In another preferred embodiment, the purification by means of chromatography is to perform primary purification by means of multimodal composite chromatography first and then perform elaborate purification by means of anion chromatography.

In another preferred embodiment, the purification by means of chromatography is to connect two multimodal chromatography resins in series and then simultaneously carry out impurity adsorption and removal and virus capture.

In another preferred embodiment, after concentration, the time of the purification treatment of the feed liquid by means of chromatography is 10 L/30 min.

In another preferred embodiment, the treatment speed of the purification by means of chromatography is 20 L of filtrate to be chromatographed/60 minutes.

In another preferred embodiment, the weight-volume ratio of the chromatographic medium and the filtrate to be chromatographed is 500 mL:10 L of filtrate.

In another preferred embodiment, the pore size of the bacterial filter is 0.2 μM.

In another preferred embodiment, the chromatographic medium is selected from: CAPTO™ Q ImpRes.

In another preferred embodiment, in the step (d), the purified recombinant lentiviral vectors have one or more of the following features:

(p1) The biological titer of the recombinant lentiviral vectors is $1.06 \times 10^9$ Tu/mL;

(p2) BSA residue<50 ng/mL;

(p3) Endotoxin<1 EU/mL.

In another preferred embodiment, before performing purification by means of chromatography, the filtrate (including concentrated or unconcentrated filtrate) is subjected to nuclease treatment.

In another preferred embodiment, the nuclease treatment includes: adding 10 U/ml nuclease and incubating it at 37° C. for 30 min.

In another preferred embodiment, in the step (b), a microfiltration hollow fiber column is used for microfiltration.

In another preferred embodiment, the microfiltration hollow fiber column is a microfiltration membrane with a cut-off value of 0.4 to 1.0 μm (preferably 0.45 to 0.8 μm).

In another preferred embodiment, in the step (c), the ratio of Vb to Vc (Vb/Vc) is 5 to 50, preferably 10 to 30, more preferably 15 to 25.

In another preferred embodiment, in the step (c), concentration is conducted through ultrafiltration.

In another preferred embodiment, the ultrafiltration adopts an ultrafiltration membrane with a cut-off value of 100 to 800 K.

In another preferred embodiment, the cut-off value of the ultrafiltration hollow fiber column is 200 to 1000 K, preferably 300 to 500 K.

In another preferred embodiment, the ultrafiltration adopts an ultrafiltration hollow fiber column and an ultrafiltration system.

In another preferred embodiment, the ultrafiltration system is selected from: AKTA flux 6 and AKTA readyflux.

In a second aspect of the present invention, a purified recombinant lentivirus prepared by the method is provided.

In a third aspect of the present invention, a preparation is provided, which comprises the purified recombinant lentivirus.

In another preferred embodiment, the preparation is a pharmaceutical composition.

In another preferred embodiment, the pharmaceutical composition also contains a pharmaceutically acceptable carrier.

In a fourth aspect of the present invention, a purification device used in the method is provided, comprising:

(S1) an optional first container for holding raw material of recombinant lentivirus to be purified;

(S2) a microfiltration unit, used for performing microfiltration treatment of the recombinant lentivirus to be purified, so as to obtain a microfiltered filtrate;

(S3) an optional concentration unit, used for concentrating the filtrate, so as to obtain a concentrated filtrate;

(S4) a chromatographic purification unit, used for purifying by means of chromatography the filtrate from the microfiltration unit or from the concentration unit, so as to obtain purified recombinant lentiviral vectors; and (S5) a collection unit, used for collecting the purified recombinant lentiviral vectors.

In another preferred embodiment, the first container, the microfiltration unit, concentration unit, the chromatographic purification unit and the collection unit are in fluid communication.

In another preferred embodiment, the chromatographic purification unit includes: a molecular exclusion chromatography unit and an anion chromatography unit.

In another preferred embodiment, the molecular exclusion chromatography unit and the anion chromatography unit are mutually independent.

In another preferred embodiment, the molecular exclusion chromatography unit and the anion chromatography unit are integrated.

In another preferred embodiment, the purification device further comprises:

(S6) a nuclease treatment unit, comprising an addition device for adding nuclease.

In another preferred embodiment, the nuclease treatment unit further comprises an incubation device for incubating a filtrate added with nuclease.

It should be understood that within the scope of the present invention, the above technical features of the present invention and the technical features described in detail below (e.g., embodiments) can be combined with each other to form new or preferred technical solutions. Due to space limitations, they are not described here.

DETAILED DESCRIPTION

After extensive and in-depth research, through mass screening and exploration of purification conditions, the inventors unexpectedly developed a fast and simple method for GMP-grade large-scale purification of recombinant lentivirus with an excellent purification effect for the first time. In the method provided by the present invention, by using specific purification media and specific purification steps and conditions, the production raw materials containing recombinant lentivirus can be purified in an extremely efficient, fast and large-scale manner, so as to obtain a recombinant lentiviral preparation with high purification, less impurities and no endotoxin. On this basis, the present invention is completed.

Terminology

As used herein, the term "composite filler resin" refers to CAPTO™ Q, CAPTO™ ImpRes and CAPTO™ DEAE.

As used herein, "composite filler resin" refers to the chromatography using composite filler resin.

As used herein, the terms "recombinant lentivirus" and "lentiviral vector" can be used in an interchangeable manner and refer to a lentiviral vector produced by introducing a specific plasmid into a specific packaging cell. Typically, these lentiviral vectors can be used in the subsequent reactions of transfecting predetermined cells (including human and non-human mammalian cells) for therapeutic or non-therapeutic purposes.

By using a GE AKTA device and a new generation of CAPTO™ Core700 and CAPTO™ adhere ImpRes resin combination (but not limited to the combination), the method illustrated in the present invention quickly obtains a high-purity lentiviral preparation.

The purified recombinant lentiviral vector preparation prepared by the method provided by the present invention can be used for the production of cellular or genetic pharmaceuticals.

The Present Invention has the Following Main Advantage:

A high-purity lentiviral preparation can be obtained quickly by combining CAPTO™ Core700 with CAPTO™ adhere ImpRes to purify lentivirus.

Below the present invention is further illustrated in conjunction with specific embodiments. It should be understood that these embodiments are intended to illustrate the present invention and not to limit the scope of the present invention. The experimental methods without specific conditions in the following embodiments are generally in accordance with conventional conditions, such as the conditions described in Sambrook et al., Molecular Cloning: Laboratory Manual (New York: Cold Spring Harbor Laboratory Press, 1989), or in accordance with the conditions recommended by the manufacturer. Unless otherwise stated, the percentages and parts are percentages by weight and parts by weight.

Embodiment 1

(1) Harvesting of a feed liquid: Collect a lentivirus feed liquid (2) Microfiltration clarification:

a) Connect a 0.45-0.8 µM microfiltration hollow fiber column to an AKTA Flux 6 system and test integrity;

b) Sterilize the AKTA Flux 6 system on line with 1M NaOH;

c) Wash the AKTA Flux 6 system with water for injection;

d) Wash the AKTA Flux 6 system with sterile 1×PBS;

e) Pour 20 L of recombinant lentivirus feed liquid into a feed liquid bucket in two batches, perform microfiltration and harvest a filtrate.

(3) Ultrafiltration concentration:

a) Connect a 300-800 K ultrafiltration hollow fiber column and an AKTA Flux 6 system and test integrity;

b) Sterilize the AKTA Flux 6 system on line with 1M NaOH;

c) Wash the AKTA Flux 6 system with water for injection;

d) Wash the AKTA Flux 6 system with sterile 1×PBS;

e) Perform ultrafiltration concentration of the microfiltered lentivirus feed liquid in the 300-800 K ultrafiltration column and the AKTA Flux 6 system and discard the filtrate;

f) Concentrate the lentivirus feed liquid from 20 L to 1~2 L.

(4) Nuclease treatment:

a) Add nuclease to 1 to 2 L of the lentivirus feed liquid at a ratio of 10 to 1000 U/mL and mix well;

b) Incubate it at 2 to 8° C. overnight.

(5) Operation of using CAPTO™ Core700 and CAPTO™ adhere ImpRes in series to remove impurities and capture virus:

a) Connect 500 mL of CAPTO™ Core700 and 500 mL of CAPTO™ adhere ImpRes in series and install them on an AKTA pure 150 chromatography system; b) Sterilize the AKTA Flux 150 system on line with 1M NaOH;

c) Wash the AKTA Flux 150 system with water for injection;

d) Wash the AKTA pure 150 system with a sterile lentivirus freezing medium;

e) Balance;

f) Load 1 to 2 L of the feed liquid, use 20 to 50 mM Tris-Cl/1 to 1.5 M NaCl for elution after the loading and collect the elution peak.

(6) Ultrafiltration and liquid exchange:

a) Connect a 300-800K ultrafiltration hollow fiber column and an AKTA Flux 6 system and test integrity;

b) Sterilize the AKTA Flux 6 system on line with 1M NaOH;

c) Wash the AKTA Flux 6 system with water for injection;

d) Wash the AKTA pure 6 system with a sterile lentivirus freezing medium;

e) Perform ultrafiltration and liquid exchange of the microfiltered lentivirus feed liquid in the 300-800 K ultrafiltration hollow fiber column and the AKTA Flux 6 system and discard the filtrate;

f) Harvest 100 to 300 mL of recombinant lentiviral vectors.

(7) Filtration sterilization, subpackaging and cryopreservation:

a) Use a 0.2 µM filter to filter the purified lentivirus feed liquid; b) Subpackage the finished product in 1 mL/tube;

c) Store the lentivirus preparation in an ultra low temperature refrigerator (≤−70° C.).

I. Results (1) Concentration of the finished lentivirus product 2~4× $10^9$/mL (2) BSA<50 ng/mL;

(3) HCP<1 ng/mL;

(4) Nucleic acid residue<5 pg/mL;

(5) RCL negativity.

II. Conclusion

Using a 0.45-0.8 µM microfiltration hollow fiber column, a 300-800 K hollow fiber column and CAPTO™ Core700+ CAPTO™ adhere ImpRes composite filler to perform clarification filtration, concentration, liquid exchange and impurity removal step by step can quickly obtain a high-purity lentivirus preparation.

All the documents mentioned in the present invention are cited as references in the present application, as if each document is individually cited as a reference. Further, it should be understood that after reading the above teaching content of the present invention, those skilled in the art can make various changes or modifications to the present invention and these equivalent forms also fall within the scope defined by the appended claims of the present application.

The invention claimed is:

1. A method for large-scale purification of recombinant viral vectors, wherein the method comprises:

(a) providing a feed liquid comprising the recombinant viral vectors, wherein the feed liquid has a volume of no less than 20 liters;

(b) carrying out a microfiltration treatment on the feed liquid to obtain a microfiltered filtrate, which comprises the recombinant viral vectors, wherein the microfiltration treatment is conducted using a microfiltration hollow fiber column, wherein the microfiltration hollow fiber column comprises a microfiltration membrane with a cut-off value of 0.4 to 0.8 μm;

(c) concentrating the filtrate to obtain a concentrated filtrate, wherein the concentrating is conducted using an ultrafiltration membrane with a cut-off value of 100 K to 800 K;

(d) purifying the filtrate by chromatography to obtain a crude product comprising the recombinant viral vectors; and (e) subjecting the crude product to liquid exchange and purification to obtain purified recombinant viral vectors;

wherein the chromatography in step (d) is selected from anion chromatography, size exclusion chromatography and multimodal composite chromatography, or combinations thereof.

2. The method according to claim 1, wherein the chromatography in step (d) comprises anion chromatography followed by multimodal composite chromatography.

3. The method according to claim 1, wherein in step (d), the purified recombinant viral vectors have one or more of the following features:

(p1) the biological titer of the recombinant viral vectors is $1.06 \times 10^9$ Tu/mL;

(p2) BSA residue<50 ng/mL;

(p3) endotoxin<1 EU/mL.

4. A purification device for performing the method of claim 1, wherein the purification device comprises:

a microfiltration unit, used for performing microfiltration treatment of the recombinant viral vectors to be purified, so as to obtain a microfiltered filtrate;

a concentration unit, used for concentrating the microfiltered filtrate, so as to obtain a concentrated filtrate; and a chromatographic purification unit, used for purifying by chromatography the concentrated filtrate, so as to obtain purified recombinant viral vectors.

5. The purification device according to claim 4, wherein the chromatographic purification unit comprises a size exclusion chromatography unit and an anion chromatography unit.

6. The purification device according to claim 4, wherein the purification device further comprises:

a nuclease treatment unit, comprising an addition device for adding a nuclease.

7. The method of claim 1, wherein the recombinant viral vectors comprise lentiviral vectors.

* * * * *